(12) United States Patent
Walters et al.

(10) Patent No.: US 7,397,238 B2
(45) Date of Patent: Jul. 8, 2008

(54) METHODS AND APPARATUS FOR INSPECTING MATERIALS

(76) Inventors: William T. Walters, #8 Curlew, LaMarque, TX (US) 77568; Xiaowen Wu, 17311 Canyon Knoll, Houston, TX (US) 77095

( * ) Notice: Subject to any disclaimer, the term of this patent is extended or adjusted under 35 U.S.C. 154(b) by 325 days.

(21) Appl. No.: 11/191,843

(22) Filed: Jul. 28, 2005

(65) Prior Publication Data
US 2007/0024278 A1 Feb. 1, 2007

(51) Int. Cl.
G01N 27/82 (2006.01)
G01N 27/72 (2006.01)
G01R 33/07 (2006.01)
G01R 33/09 (2006.01)

(52) U.S. Cl. .................. 324/240; 324/228; 324/238; 324/252; 324/207.2; 324/207.21

(58) Field of Classification Search ......... 324/238–242, 324/251–252, 207.2, 207.21, 228; 338/32 R, 338/32 H; 73/514.31, 514.39
See application file for complete search history.

(56) References Cited

U.S. PATENT DOCUMENTS

| | | | |
|---|---|---|---|
| 2,467,306 A | 4/1949 | Habig |
| 3,930,404 A | 1/1976 | Ryden, Jr. |
| 3,955,425 A | 5/1976 | Corneau |
| 4,027,527 A | 6/1977 | Bennett et al. |
| 4,041,773 A | 8/1977 | Hauldren et al. |
| 4,196,607 A | 4/1980 | Youtsey et al. |
| 4,445,088 A | 4/1984 | Schubel |
| 4,492,115 A | 1/1985 | Kahil et al. |
| 4,510,447 A | 4/1985 | Moyer |
| 4,555,665 A | 11/1985 | Stanley et al. |
| 4,602,212 A | 7/1986 | Hiroshima et al. |
| 4,611,170 A | 9/1986 | Stanley et al. |
| 4,629,991 A | 12/1986 | Wheeler |
| 4,636,727 A | 1/1987 | Kahil et al. |
| 4,675,604 A | 6/1987 | Moyer et al. |
| 4,677,379 A | 6/1987 | Arnaud et al. |
| 4,704,580 A | 11/1987 | Moake et al. |
| 4,710,712 A | 12/1987 | Bradfield et al. |
| 4,725,963 A | 2/1988 | Taylor et al. |
| 4,792,756 A | 12/1988 | Lam et al. |
| 4,823,082 A | 4/1989 | Nasu et al. |
| 4,934,179 A | 6/1990 | Biggerstaff |
| 4,945,306 A | 7/1990 | Lowther |
| 5,004,724 A | 4/1991 | De |
| 5,008,621 A | 4/1991 | Jiles |
| 5,030,911 A | 7/1991 | Lam |
| 5,059,903 A | 10/1991 | Otaka et al. |
| 5,140,265 A | 8/1992 | Sakiyama et al. |
| 5,245,279 A | 9/1993 | Bendzsak |
| 5,256,965 A | 10/1993 | Nomura |
| 5,258,708 A | 11/1993 | Sadeghi et al. |

(Continued)

*Primary Examiner*—Bot LeDynh
(74) *Attorney, Agent, or Firm*—Jeffrey L. Wendt; Pramudji Wendt & Tran, L.L.P.

(57) ABSTRACT

Apparatus and methods for inspecting materials such as cylindrical and tubular members are disclosed. One apparatus includes a frame that supports a magnetic coil and a detector assembly, the detector assembly having one or more magnetic detectors adapted to be spaced a first distance from the material being inspected by one or more substantially frictionless members. This abstract allows a searcher or other reader to quickly ascertain the subject matter of the disclosure. It will not be used to interpret or limit the scope or meaning of the claims.

23 Claims, 9 Drawing Sheets

U.S. PATENT DOCUMENTS

| | | | |
|---|---|---|---|
| 5,303,592 A | 4/1994 | Livingston |
| 5,336,998 A | 8/1994 | Watts et al. |
| 5,424,640 A | 6/1995 | Levy |
| 5,430,376 A | 7/1995 | Viertl |
| 5,479,100 A | 12/1995 | Fowler et al. |
| 5,532,591 A | 7/1996 | Logue |
| 5,537,035 A | 7/1996 | Fowler et al. |
| 5,537,038 A | 7/1996 | Ando |
| 5,581,037 A | 12/1996 | Kwun et al. |
| 5,600,069 A | 2/1997 | Girndt et al. |
| 5,619,136 A | 4/1997 | Drury |
| 5,670,578 A | 9/1997 | Shawl |
| 5,671,155 A | 9/1997 | Edens et al. |
| 5,675,251 A | 10/1997 | MacLean et al. |
| 5,747,998 A | 5/1998 | Fowler et al. |
| 5,751,144 A | 5/1998 | Weischedel |
| 5,914,596 A | 6/1999 | Weinbaum |
| 5,943,632 A | 8/1999 | Edens et al. |
| 6,014,024 A | 1/2000 | Hockey et al. |
| 6,014,091 A | 1/2000 | Notlemeyer et al. |
| 6,057,684 A | 5/2000 | Murikami et al. |
| 6,087,830 A | 7/2000 | Brandly et al. |
| 6,150,809 A | 11/2000 | Tiernan et al. |
| 6,172,501 B1 | 1/2001 | Tsukada et al. |
| 6,356,072 B1 | 3/2002 | Chass |
| 6,498,451 B1 | 12/2002 | Boules et al. |
| 2003/0112006 A1 | 6/2003 | Luetzow |
| 2004/0006437 A1 | 1/2004 | Lam et al. |

METHODS AND APPARATUS FOR INSPECTING MATERIALS

BACKGROUND OF THE INVENTION

1. Field of Invention

The present invention relates generally to the field of inspection, and more specifically to apparatus and methods of using same for inspection of materials such as cylindrical and tubular members.

2. Related Art

Inspection of metal pipe or solid tubular members by magnetic means conventionally involves magnetizing the member to create a magnetic field which extends circumferentially and is characterized by lines of magnetic flux which extend either axially of the tubular member or generally perpendicular to its axis, dependent on the manner by which magnetism is induced. In many of the present systems, current flow through a wire coil positioned about the tubular member forms magnetic lines of flux through the opening of the coil which extend axially of the member under inspection. In other systems, current flows axially of the tubular member within the wall thereof so as to create a magnetic field, the lines of flux of which extend circumferentially about the tubular member in an orientation substantially perpendicular to the tubular member. The presence of structural flaws or anomalies in the wall of the tubular member, such as surface nicks or pits, cracks, voids, or various crystalline discontinuities, disturbs the uniformity of a magnetic field in the wall of the tubular member. Accordingly, the structural integrity of the tubular member and its relative freedom of such flaws may be inspected by sensing and detecting the magnetic field variations with sensors disposed closely adjacent the surface of the tubular member.

The sensing of variations in a magnetic field in a pipe wall is customarily achieved by passing or moving an induction coil or similar device through the magnetic field and any magnetic field variations to induce voltages in the coil indicative of the magnetic field variations. The voltages or voltage signals may then be transmitted to appropriate recording and processing equipment. For optimum detection sensitivity and for detection of very small cracks in a pipe wall which can be a few thousandths of an inch in depth, it is necessary that the detecting or sensor coil be placed closely adjacent the exterior surface of the tubular member. Normally the adjacent coil is disposed from 0.002 inches (0.051 mm) to 0.020 inches (0.51 mm) relative the surface of the tubular member with an axis of the coil substantially perpendicular to the surface. The sensor coils are mounted in a support, conventionally referred to as a sensor shoe, which is provided with contact surfaces adapted to contact with the surface of the tubular member in a manner so that the sensing coil is supported closely adjacent the surface of the tubular member at an optimum distance or spacing. Normally, the coil is protected from direct contact with the surface of the pipe by means of a thin shim of magnetically transparent material.

Inspecting the surface of the tubular members requires that the inspection sensor be moved along the surface in a predetermined inspection path. In one widely used pipe inspection apparatus, a plurality of sensor shoes are applied to the surface of the pipe in circumferential spacing thereabout and each of the sensor shoes is moved relatively to the pipe in a circumferential helical path whereby the plurality of sensors provides more than 100 percent coverage of the pipe surface. The relative movement may be effected by moving the sensors longitudinally while rotating the sensor shoes around a stationary pipe or the pipe can be moved longitudinally while the sensors are rotated about the pipe. In any event, there is relative sliding movement between the sensor shoes and the pipe surface, which causes wear of the contact surfaces of a sensor shoe by extensive use. The shim also can come into contact with the pipe and can be similarly eroded. The wearing down of the contact surfaces and shim results in the coils being supported from the pipe surface inside the optimum spacing range or possibly being damaged by eventual contact with the pipe. When either event occurs, a new sensor shoe is required.

Furthermore, sensor shoes are customarily designed for use with a specific diameter of pipe, and the contact surfaces of a sensor shoe are fixed in a permanent orientation such that when placed in contact with the surface of the pipe, the sensing coil is positioned for optimum detection sensitivity. Accordingly, a given sensor shoe is designed for inspection of only one diameter of pipe and is inappropriate for use as an inspection sensor for pipes of a different diameter since for such pipe diameters the sensing coil is supported at other than an optimum distance from the surface to be inspected.

When a typical oil well is drilled, a casing is installed to prevent cave-in, the casing extending from the earth's surface to the bottom of the well. To convey fluid from the formation to the surface, a string of tubing (typically jointed or coiled tubing) is typically run inside the casing. A device referred to as a sucker rod pump may be employed to remove the oil and. Sucker rod pumps may be anchored within a lower end of the tubing and the pump reciprocated by means of a string of sucker rods extending from the earth's surface. Sucker rods are typically formed of steel and may be installed by means of couplings that are attached between threaded ends of the rods. A typical sucker rod may, for instance, be of about 25 feet in length with a coupling between each length of rod. The sucker rods reciprocate within tubing which typically may be 2-4 inches in internal diameter. Very few pumped oil wells are perfectly vertical. If an oil well is not perfectly vertical the sucker rods tend to slide against the interior surface of the tubing, and if the couplings are of larger diameter than the sucker rods, vertical reciprocation of sucker rod couplings against the interior surface of tubing may be detrimental both to the coupling and to the tubing itself. Couplings may wear causing the sucker rods to separate, or a hole can be worn in the tubing, with consequential decrease of oil production to the earth's surface. Whipping of sucker rods against the internal surface of the tubing may occur, which may be detrimental to the rods, the rod couplings, and the tubing. For these and other reasons, some operators provide stabilizers on the exterior of sucker rods to prevent excess wear of sucker rod couplings and the interior of the tubing. Currently there is no known apparatus or method for inspecting the sucker rods in terms of cracks or corrosion, except for taking the sucker rods to a shop, which usually requires compete disassembly of the sucker rod string.

The presence of paraffin may be another problem encountered in pumping oil wells. If the paraffin can be maintained in solution in the crude oil, the oil may be pumped without significant problem. However, in cold regions, or in wells wherein the surface temperature is much lower than the downhole temperature, paraffin may solidify on he internal walls of the tubing, and may actually stop flow completely. For this reason, many operators install so-called paraffin scrapers on sucker rods for scraping at intervals equal to or slightly less than the stroke of the pump jack to keep the walls of the tubing from closing in to the point that fluid flow is restricted. There are many scraper designs, but all present the same problem as sucker rod couplings from the standpoint of inspection of the sucker rods. Current inspection methods and apparatus are not adequate for in situ inspection.

From the above it is evident that there is a need in the art for improvements in tubular member inspection methods and apparatus.

SUMMARY OF THE INVENTION

In accordance with the present invention, apparatus and methods are described that reduce or overcome problems in previously known apparatus and methods.

One aspect of the present invention is a tubular member inspection apparatus comprising:
 (a) a frame;
 (b) a magnetic coil and a detector assembly supported by the frame;
 (c) the frame, magnetic coil, and detector assembly each having inlet and outlet openings for passing a tubular member there through, the detector assembly having one or more magnetic detectors adapted to be spaced a first distance from the tubular member by one or more substantially frictionless members during an inspection.

Apparatus of the invention may comprise an actuator assembly comprising sensors adapted to sense wide portions of the tubular member and direct one or more actuators in the detector assembly to retract the detectors away from the tubular member a second distance greater than the first distance. Apparatus of the invention include those wherein the first distance is at least 0.030 inch (0.076 cm), and those apparatus wherein the first distance ranges from about 0.050 inch (0.127 cm) up to about 0.5 inch (1.27 cm). Other apparatus of the invention are those wherein the detector assembly comprises a plurality of detector support sub-assemblies. While the invention is not so limited, each detector support sub-assembly may comprise a primary and a secondary support member and one of the actuators, the primary support member adapted to support the one or more magnetic detectors, the primary support member moveably connected to the secondary support member through a dual linkage. The dual linkage may allow the detectors to move substantially parallel to the tubular member when retracting away from and toward the tubular member. Other apparatus of the invention are those wherein the first distance is maintained by one or more precision rollers held in each primary support, and those wherein each actuator is the same or different and selected from pneumatic, hydraulic, and electronic actuators. The dual linkage may comprise first and second links, each link having first and second ends, the first ends individually connected to the primary support member at first and second connections, and the second ends individually connected to the second support member at third and fourth connections. The connections allow pivot movement between the links and the support members. Apparatus of the invention allow movement of the detectors away from the tubular member being inspected, the second distance being sufficient to avoid damage to the detectors. The sensors of the actuator assembly may comprise a first rotating member riding on the tubular member upstream of the detector assembly and a second rotating member riding on the tubular member downstream of the detector assembly. Alternatively, the sensors of the actuator assembly may be optical sensors. The plurality of detector support sub-assemblies may comprise alternating outer detector support sub-assemblies and inner detector support sub-assemblies, wherein the outer detector support sub-assemblies each support a transverse magnetic detector and a wall thickness detector. This arrangement of inner and outer detector support sub-assemblies (creating what is sometimes referred to herein as a "dual ring" of detectors) is one possible arrangement, allowing the detectors to monitor magnetic flux lines that, together, will cover more than 360 degrees of the circumference of the tubular member, therefore guaranteeing 100 percent inspection, and thus the ability to detect defects in tubular members. However, all detector sub-assemblies may be identical and provide for a single ring of detectors around the tubular member during inspection. The latter arrangement may not find a defect if it exists in between the detectors, and cannot therefore guarantee full 100 percent coverage of the tubular member, and may be less sensitive in detecting defects than dual ring embodiments, however it is still quite sensitive and experience users will find the unit useful. The magnetic detectors may be selected from Hall elements, magneto diodes, magneto resistors, and the like, although the invention is not so limited. The inner detector support sub-assemblies may each support a transverse magnetic detector, and these may also be selected from Hall elements, magneto diodes, magneto resistors, and the like. The actuator assembly may comprise first and second valves, the first valve positioned upstream of the detector assembly and the second valve positioned downstream of the detector assembly. In certain embodiments the first and second valves are each spring-loaded, and each valve may comprise a pressurized fluid inlet and a bleed fluid exhaust outlet, wherein the fluid may be air, nitrogen, hydraulic fluid, or some other fluid, although air is generally available at lower cost. The sensors may be mounted on slide mechanisms adapted to slide into a position allowing a lever to bleed the fluid through the bleed fluid exhaust outlet when a wide portion of tubular member is sensed by one of the sensors. The valves may be adapted to allow pressurized fluid into the actuators when the sensors do not sense a wide portion of tubular member. These embodiments may include an electronic circuit or pneumatic means to synchronize the resetting of the fluid pressure in the actuators after the wide portion of tubular member has passed by the detectors and when the second sensor is reached. In certain embodiments, the frame may include an end piece having a curved profile, allowing the apparatus to be tilted when inspecting vertical tubular members.

Another aspect of the invention are magnetic detector and support sub-assemblies comprising:
 (a) a primary support member;
 (b) a magnetic detector supported by the primary support member;
 (c) a secondary support member; and
 (d) an actuator, wherein the primary support member is moveably connected to the secondary support member through a dual linkage and the actuator, the dual linkage allowing the detector to be positioned substantially parallel to a material being inspected when moved away from and toward the material by action of the actuator.

Another aspect of the invention are methods of inspecting a tubular member, in general comprising:
 (a) passing a tubular member through an apparatus comprising
  (i) a frame;
  (ii) a magnetic coil;
  (iii) a detector assembly; and
 (b) detecting variations in the magnetic field produced by defects in the tubular member, the detector assembly having one or more magnetic detectors spaced a first distance from the tubular member by one or more substantially frictionless members during inspection.

Optionally, methods of the invention include sensing a wide portion of the tubular member and directing one or more actuators in the detector assembly to retract the detectors away from the tubular member a second distance greater than the first distance.

Apparatus and methods of the invention may be employed by passing a tubular member through a stationary apparatus of the invention, or the apparatus of the invention may be moved along a stationary tubular member. Apparatus and methods of the invention will become more apparent upon review of the brief description of the drawings, the detailed description of the invention, and the claims that follow.

BRIEF DESCRIPTION OF THE DRAWINGS

The manner in which the objectives of the invention and other desirable characteristics can be obtained is explained in the following description and attached drawings in which.

It is to be noted, however, that the appended drawings are not to scale and illustrate only typical embodiments of this invention, and are therefore not to be considered limiting of its scope, for the invention may admit to other equally effective embodiments.

DETAILED DESCRIPTION

In the following description, numerous details are set forth to provide an understanding of the present invention. However, it will be understood by those skilled in the art that the present invention may be practiced without these details and that numerous variations or modifications from the described embodiments may be possible.

All phrases, derivations, collocations and multiword expressions used herein, in particular in the claims that follow, are expressly not limited to nouns and verbs. It is apparent that meanings are not just expressed by nouns and verbs or single words. Languages use a variety of ways to express content. The existence of inventive concepts and the ways in which these are expressed varies in language-cultures. For example, many lexicalized compounds in Germanic languages are often expressed as adjective-noun combinations, noun-preposition-noun combinations or derivations in Romanic languages. The possibility to include phrases, derivations and collocations in the claims is essential for high-quality patents, making it possible to reduce expressions to their conceptual content, and all possible conceptual combinations of words that are compatible with such content (either within a language or across languages) are intended to be included in the used phrases.

The present invention is directed toward solving or alleviating problems in inspection of tubular members, in particular pipe, tubing, sucker rods, and the like used in the petroleum production and petrochemical industries. One problem frequently encountered in magnetically inspecting these materials for defects is that the sensors that ride on the tubular member being inspected become damaged and need to be replaced frequently. Another problem is that pipe, tubing, sucker rods, and the like may be coupled together in sections, and the coupling is larger than the overall diameter of the pipe, tubing, sucker rod or other tubular member. There may also be debris present, such as paraffin, on the tubular member. Previously known magnetic inspection apparatus provide magnetic detectors that ride very close to the surface of the tubular member with no way to move them quickly and dynamically during the inspection process, so that the couplings and/or solidified debris often get caught in the magnetic heads and pull the assemblies apart. Apparatus and methods of the invention address these problems by providing substantially frictionless members that space the magnetic detectors away from the surface of the tubular member a first, known distance. Optionally, actuator assemblies are provided, which allow the detector assemblies to move away from the tubular member a second distance greater than the first distance before the detectors can be damaged. The actuator assemblies may comprise two valve packages, located one at one end of the apparatus, and one located at the opposite end, with the detector assembly in between. The valves may be spring loaded and have air or other fluid pressure feeding into them and an open bleed port for exhaust. When contact wheels associated with each valve are both riding normally on the tubular member surface, both valves will have fluid pressure feeding to the detector array assembly, effectively closing the arms onto the surface of the tubular member. When a coupling or other obstruction comes toward one of the actuator assemblies from either end, in some embodiments a contact wheel attached to an actuator slide mechanism is slid backward in the actuator assembly (due to the larger diameter of the coupling or debris on the tubular member) and an actuator lever will trip the bleeder valve releasing fluid pressure and immediately opening the detector array assembly allowing the larger coupling or debris to freely pass through the inventive apparatus without damage. When the coupling and/or debris contacts the wheel on the next actuator assembly it also slides backward and resets the fluid source to all cylinders in the detector assembly, closing the arms back onto the tubular member surface. A small electronic circuit or all pneumatic means may be used to monitor the timing between the two valves and to synchronize their action.

The dual linkage detector assembly is an important feature of the inventive apparatus. The dual linkage facilitates positioning of the detectors on a substantially parallel axis to the tubular member. Currently known apparatus use a single pivot point which does not allow the detectors to be positioned in a precise manner. They are consistently at odd angles and off axis to the center of the tubular member. Another feature of the inventive apparatus is the provision of one or more substantially frictionless members, which may be two roller bearings, for each detector carrying arm, to help maintain a precise air gap between the detectors and the tubular member surface. The substantially frictionless members may benefit users of the inventive apparatus in one or more of the following ways: reduced wear of the magnetic detectors, which can save the user time and money; reduced (and in some cases, totally overcome) magnetic noise from the surface of the tubular member; and signal to noise relationships that allow digital electronics to produce better signal processing. The precise air gap means reduced noise from the tubular member surface, and the quality of signals may be completely independent of inspection speed. Digital signal processing software, known under the trade designation Digi-Pro™, available from Scan Systems Corp, Houston, Tex., allows 100 percent of the inspection signal to be digitized and processed within a computer. The computer and digital signal processing software known under the trade designation Digi-Pro™ may utilize a series of virtual printed circuit boards known under the trade designation SimKardz™ to perform the calculations required. Signals may be captured from the detectors and digitized almost immediately, then processed through one or more algorithms to produce large signal to noise ratios. Improvements in signal to noise ratios of at least 20 percent, sometimes at least 100 percent, and in certain embodiments even 200 percent have been seen, compared with existing industry standard equipment.

Hall Element devices may be used to sense the electrical shift in voltage during the inspection methods of the invention; however, there could be any number of different sensing technologies that could be used in the inventive apparatus, such as magneto diodes and magneto resistors.

The inventive apparatus also allows a user to use the same machine and overall system to perform the same inspections on tubing and sucker rod assemblies coming from a well bore, which up to now has not been considered.

Apparatus of the invention may be incorporated into larger units, within pipe plants, as well as into well head inspection equipment.

Given that production time and safety are primary concerns, and that there is considerable investment in existing equipment, apparatus and methods of the invention present an advance in the art since existing apparatus may be modified to increase safety and efficiency during the inspection procedures, with minimal interruption of other well operations.

Figure 1:
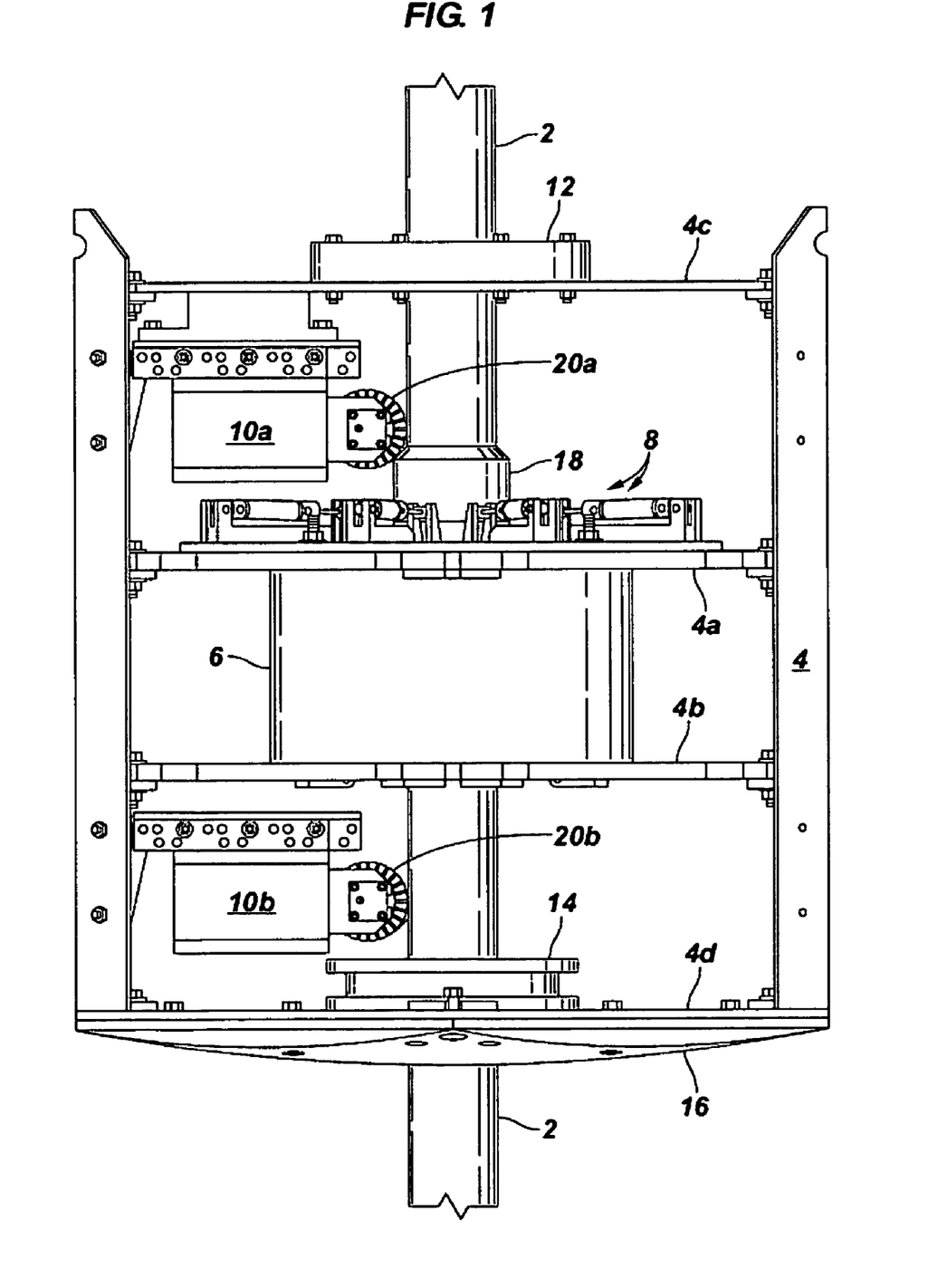
FIG. 1 is a schematic side elevation view of an apparatus of the invention.

Referring now to the figures, FIG. 1 illustrates schematically and not to scale a side elevation view of one apparatus of the invention as it may be used at a well head. The apparatus illustrated in FIG. 1 and variations thereof are known under the trade designation CenteRIDE. In FIG. 1 there is illustrated a tubular member 2 (not a part of the invention) being guided through a frame 4. Frame 4 includes in this embodiment frame sub-components 4a, 4b, 4c, and 4d, it being understood that other frames useful in the invention could have less or more components. Frame sub-components 4a and 4b serve as supports for a magnetic coil 6 and a detector assembly 8, as further detailed herein. Also illustrated are two optional actuator assemblies 10a and 10b, more further explained with reference to FIG. 2. Flanges or end pieces 12 and 14, each having inlets and outlets for tubular member 2, are provided, as well as a frame end piece 16 having an optional curved surface. The curved surface is useful when the tubular member is not being moved exactly vertically through the apparatus, and it is desirous to tilt the apparatus slightly. FIG. 1 also illustrates a wide region 18 of tubular member 2, which may either be a coupling as shown here, or debris such as paraffin, or a paraffin scraper in the case where tubular member 2 is a sucker rod. A first wheel 20a accompanying valve actuator 10a is illustrated just encountering wide region 18. In situations where tubular member 2 is being pulled upwards, a companion wheel 20b associated with valve actuator 10b has already encountered wide region 18 and instructed detector assemblies 8 to retract away from tubular member 2 to allow wide region 18 to pass through the apparatus. When wheel 20a returns to a point where it touches wide region 18 of tubular member 2, it will in turn cause detector assembly 8 to reposition the magnetic detectors in detector assembly 8 near the tubular member to proceed with inspection.

Figure 2:
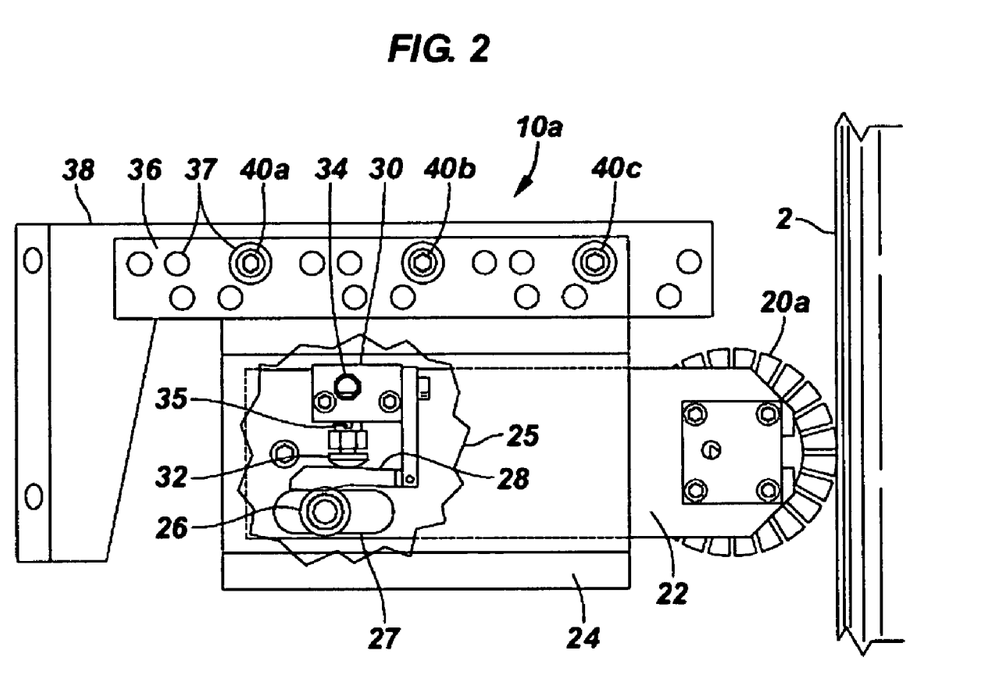
FIG. 2 is schematic side elevation view, with parts broken away, of one actuator embodiment of the invention.

FIG. 2 is schematic side elevation view, with parts broken away, of actuator valve 10a of FIG. 1. (The same numerals are used throughout the drawing figures for the same parts unless otherwise indicated.) Illustrated in FIG. 2 is a contact wheel 20a riding on a tubular member 2. Contact wheel 20a is supported by a slide bracket 22 adapted to slide within a sheath 24. A portion 25 of sheath 24 is broken away to allow viewing an actuator roller 26, a track slot 27, a bleeder valve 30 having a plunger 32, an air or other motive fluid supply port 34, and an exhaust port 35. Normally there would be a plastic or other conduit for supplying the motive fluid to port 34, but this is not shown for clarity. There may also be another conduit attached to the bleed port 35. Actuator roller 26 is attached to slide bracket 22 and is adapted to slide within track slot 27 in sheath 24. When a wide region of tubular member 2 is encountered by contact wheel 20a, slide bracket 22 and actuator roller 26 move to the left in FIG. 2. Actuator roller 26 encounters a wide end of a bleed actuator 28, which rises, and in turn pushes up on plunger 32. This action results in bleeding air or other motive fluid from bleed port 35 of bleeder valve 30, and also results in air cylinders or other mechanisms retracting magnetic detectors away from tubular member 2, as further explained in reference to FIGS. 3-7. Sheath 24 may be supported by a bracket 36, which may be a separate component or integral with sheath 24. Bracket 36 may have a series of through holes 37, allowing bolts or other fasteners 40a, 40b, and 40c to hold bracket 36 to a companion bracket 38, which may be part of frame 4.

There are many varieties of actuator assemblies useful in the invention. Any and all known actuators and methods of using them are foreseeable functional equivalents and considered useful in practicing the various aspects of the invention. The type and capacity of the actuator will vary depending on the actuation method used. Optical sensors, laser sensors, proximity switches, and the like are but a few functional equivalents.

Figure 3:
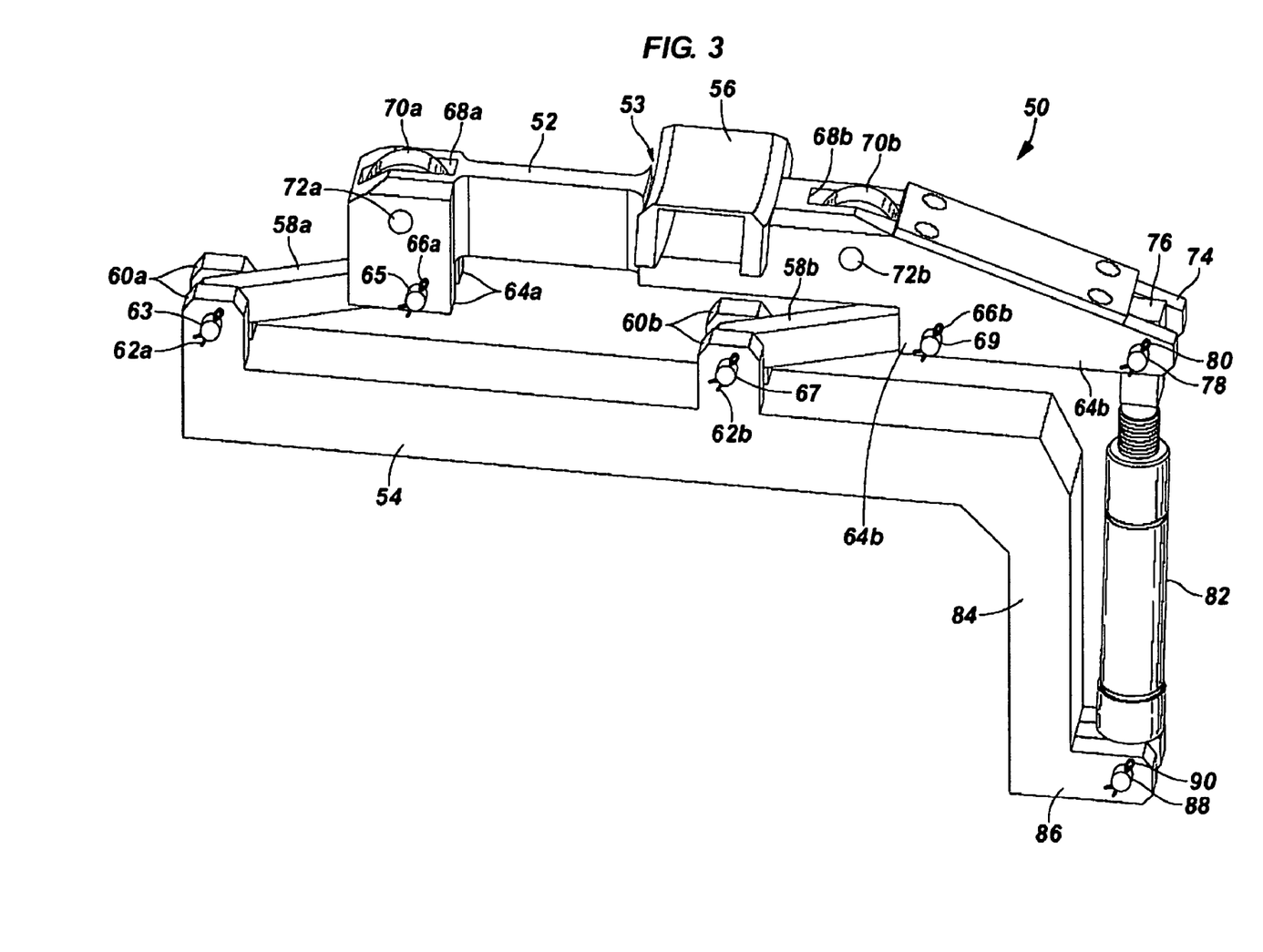
FIG. 3 is a perspective view of one possible inner arm assembly useful in the apparatus and methods of the invention.

FIG. 3 is a perspective view of one possible inner arm assembly 50 useful in the apparatus and methods of the invention. Illustrated in FIG. 3 is a primary support member 52 and a secondary support member 54. Primary support member 52 includes a slot 53 for holding a magnetic detector 56, which may be a Hall Element or other magnetic detector. Primary support member 52 may be moveably connected to the secondary support member through a dual linkage comprising first and second links 58a and 58b, each link having first and second ends, the first ends individually connected to primary support member 52 at first and second tongue and groove connections 64a an 64b, and the second ends individually connected to the second support member at third and fourth tongue and groove connections 60a and 60b. The connections allow pivot movement between links 58a and 58b and support members 52 and 54. The dual linkage may allow detector 56 to be positioned substantially parallel to the tubular member when retracting away from and toward the tubular member. Link 58a is illustrated connected to secondary support member 54 through a pin 63 secured by a cotter pin 62a, and to primary support member 52 using a pin 65 and cotter pin 66a Similarly, link 58b is illustrated connected to secondary support member 54 through a pin 67 secured by a cotter pin 62b, and to primary support member 52 using a pin 69 and cotter pin 66b.

Embodiment 50 of FIG. 3 also shows slots 68*a* and 68*b* in primary support member 52 for positioning substantially frictionless members such as rollers 70*a* and 70*b*, respectively. The substantially frictionless members could be any type of mechanism as long as it serves the function of maintaining the distance of the magnetic detectors a certain distance from the tubular member being inspected, and are substantially frictionless and/or wear-resistant so that frequent replacement is not necessary. Examples include precision metal rollers, metal ball bearings, plastic rollers, ceramic balls, non-rotating spacers in ball or roller shape, and the like. Whatever form they take, and whatever material they are composed of, the substantially frictionless members have diameter sufficient to maintain magnetic detector 56 a certain distance away from the tubular member being inspected. Further illustrated in embodiment 50 of FIG. 3 is a tongue and groove connection 74 which accepts an end 76 of an actuator 82. A pin 78 and a cotter pin 80 may be used to secure end 76 to connector 74. An opposite end of actuator 82 is secured to a section 84 of secondary support member 54 extending substantially perpendicular to a tubular member being inspected, using another a tongue and groove connector 86, including a pin 88 and a cotter pin 90. Each actuator 82 may be the same or different and selected from pneumatic, hydraulic, and electronic actuators. Apparatus of the invention allow movement of the magnetic detectors 56 away from the tubular member being inspected, the second distance being sufficient to avoid damage to the detectors.

Figure 4:
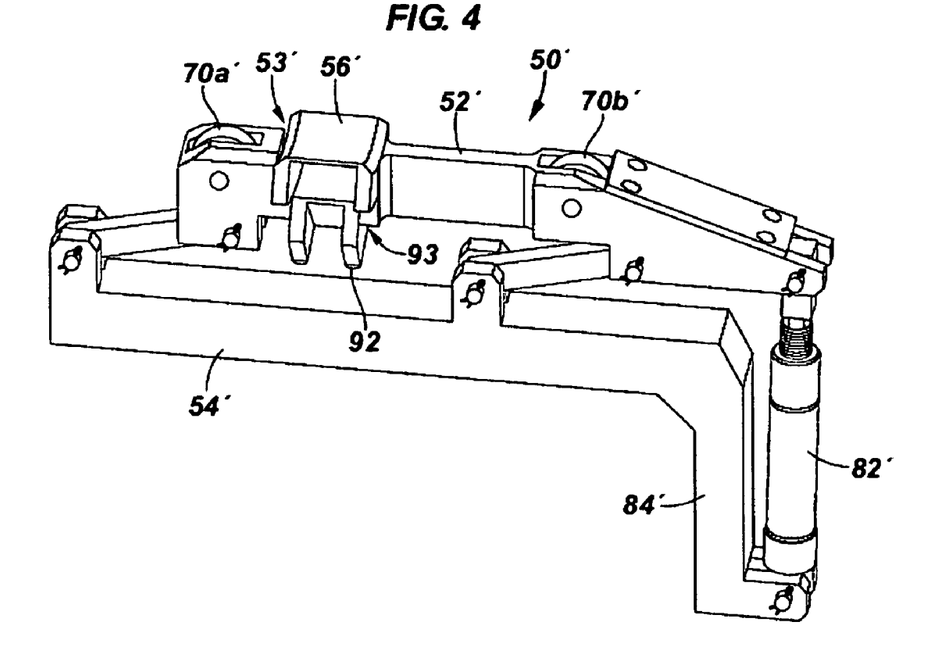
FIG. 4 is a perspective view of one possible outer arm assembly useful in the apparatus and methods of the invention, illustrated in open position.

FIG. 4 is a perspective view of one possible outer arm assembly useful in the apparatus and methods of the invention, illustrated in open position. Many components of the outer arm assembly may be the same as the inner arm assembly illustrated in FIG. 3. Outer arm assembly 50' includes a primary support member 52', a secondary support member 54', a slot 53' for holding a magnetic detector 56', as well as rollers 70*a*' and 70*b*'. An actuator 82' is secured to a section 84' of secondary support member 54' extending substantially perpendicular to a tubular member being inspected. One difference in the inner and outer arm assemblies is the provision in the outer arm assemblies of a second slot 93 and second magnetic sensor 92. Second magnetic sensor 92 may be used for inspecting wall thickness of the tubular member being inspected.

Figure 5:
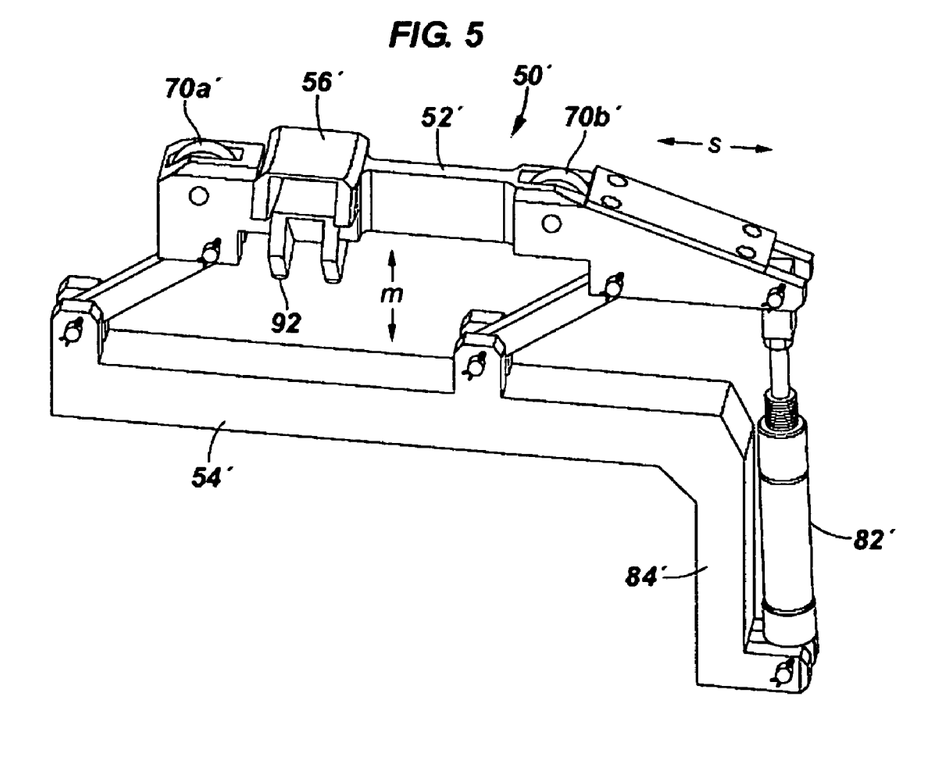
FIG. 5 is a perspective view of the outer arm assembly of FIG. 4 illustrated in closed position.

FIG. 5 is a perspective view of the outer arm assembly of FIG. 4 illustrated in closed position, in other words, in position to inspect a tubular member. A double-headed arrow denoted "m" illustrates the movement of primary support member 52' away from secondary support member 54', while arrow denoted "s" illustrates the ability to position sensors 56' and 92 substantially parallel to the tubular member being inspected.

Figure 6:
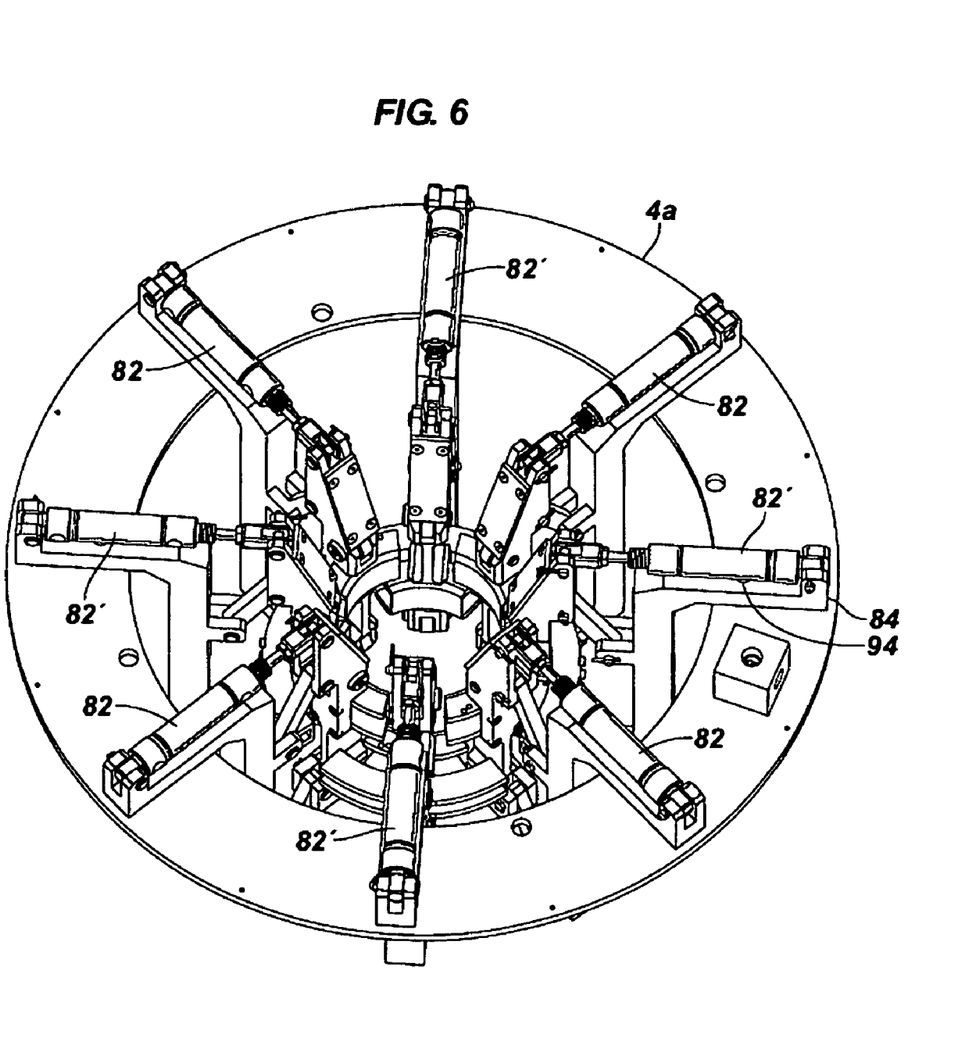
FIG. 6 is a perspective view of one possible detector assembly in accordance with the invention.
Figure 7:
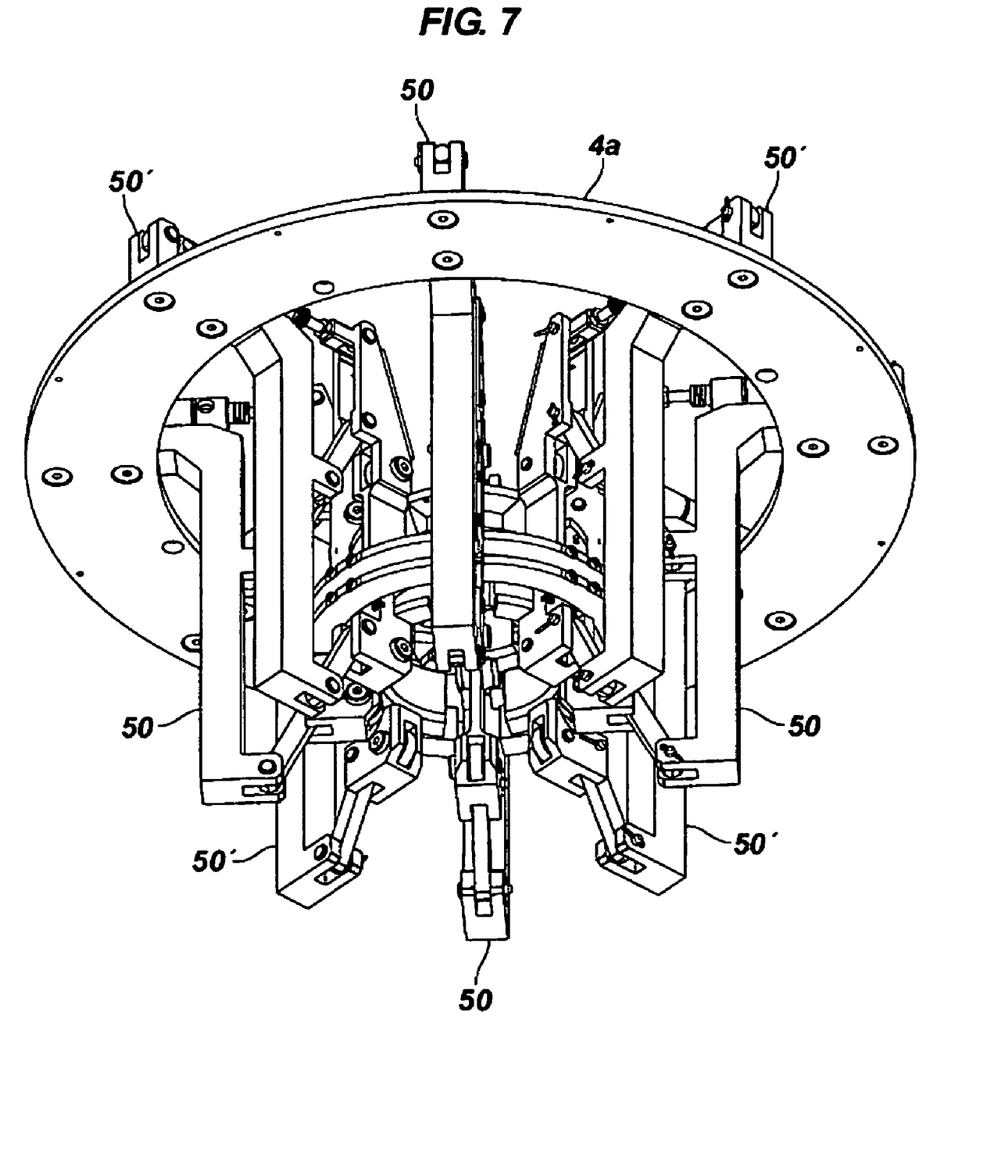
FIG. 7 is a reverse perspective view of the detector assembly illustrated in FIG. 6.
Figure 12:
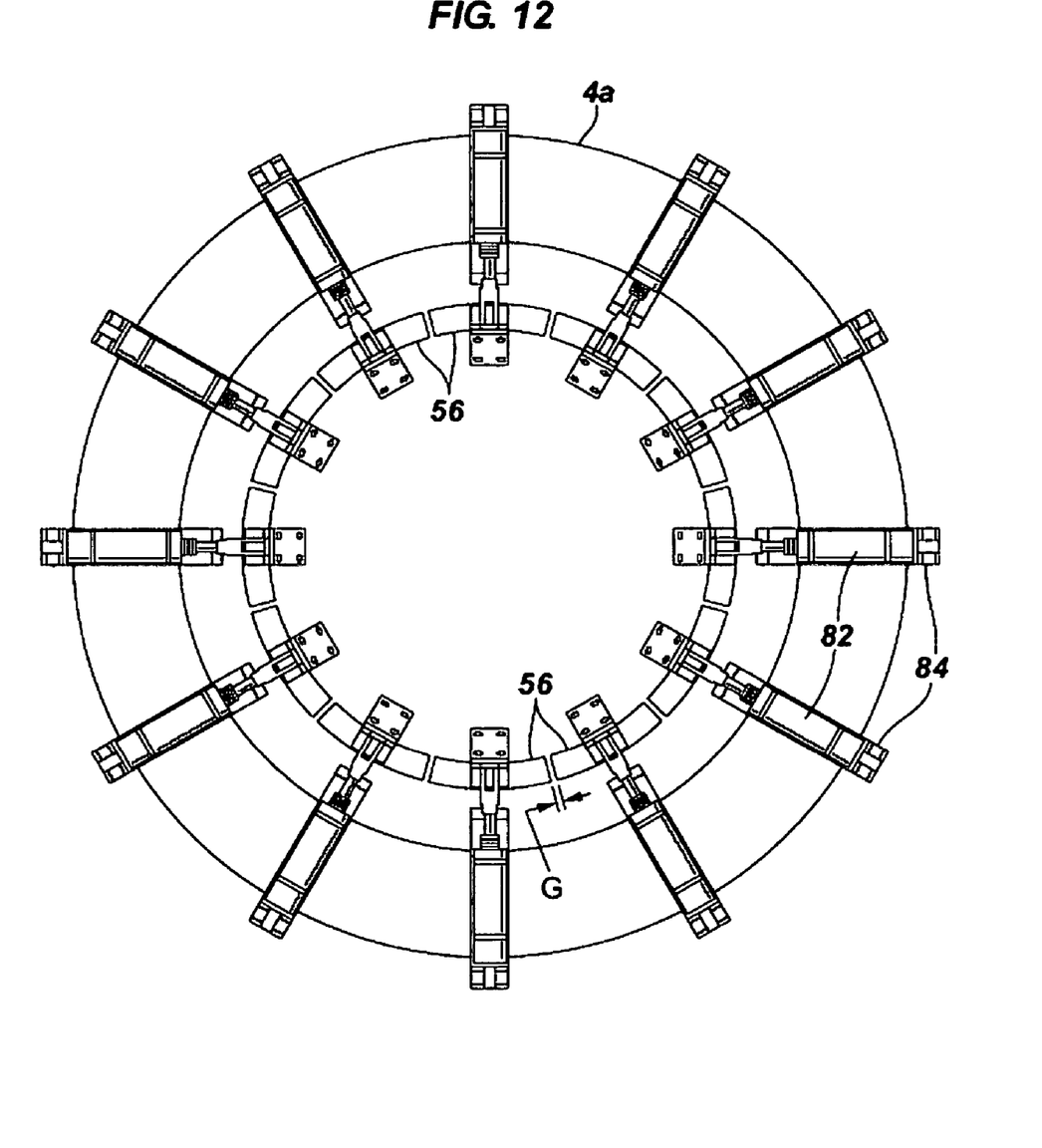
FIG. 12 is an end elevation view of another embodiment of the invention.
Figure 13:
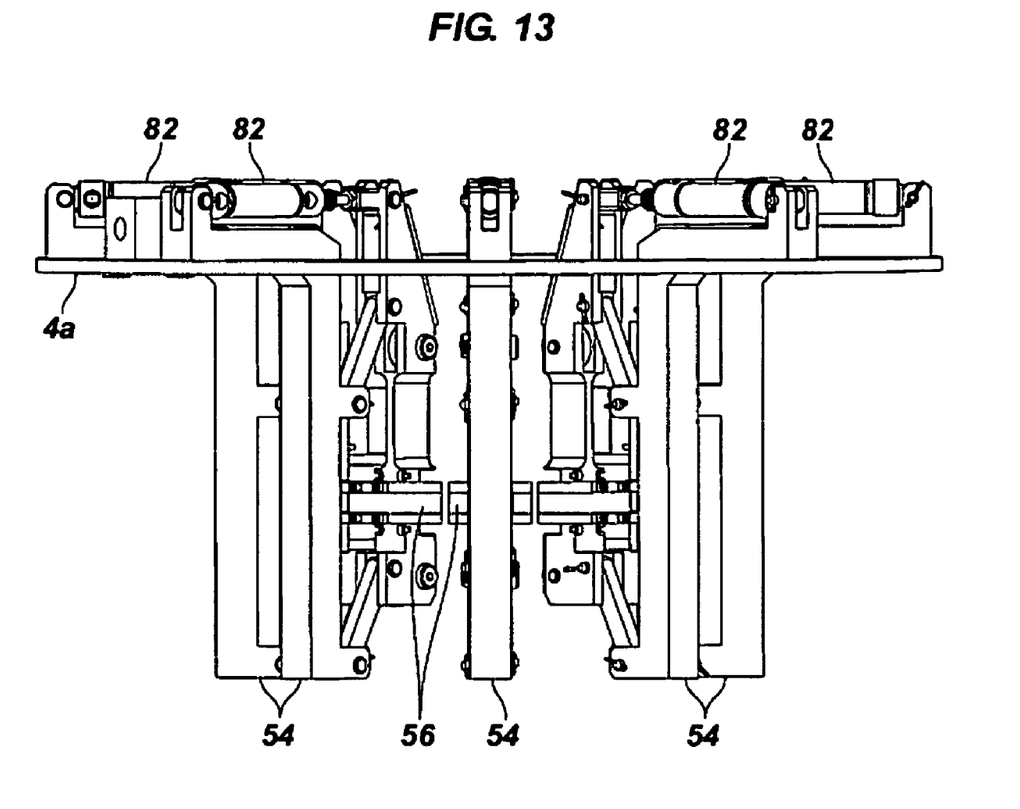
FIG. 13 is a side elevation view of the embodiment of FIG. 12.

FIG. 6 is a perspective view of one possible detector assembly in accordance with the invention. Illustrated in FIG. 6 is frame component 4*a*, partially in phantom, so that the relative positions of the various support arms may be seen. Shown are four inner support arm assemblies and their corresponding actuators 82, and four outer support arm assemblies and their corresponding actuators 82'. The arrangement of inner and outer detector support sub-assemblies is one possible arrangement, allowing the detectors to monitor magnetic flux lines without gaps between flux lines from any two detectors during an inspection procedure, therefore providing a minimum of 100 percent coverage of any tubular member being inspected. (This is in contrast to embodiments of the invention such as illustrated in FIGS. 12 and 13, discussed below.) All inner and outer support arm assemblies illustrated in FIG. 6 are in the open position. From this view it is possible to see that a tubular member passing through the detector assembly of an inventive apparatus during an inspection method (or an inventive apparatus being driven past a stationary tubular member) would receive a substantially complete magnetic inspection of its surface and wall thickness upon movement of the detector assemblies to the closed position. This view also illustrates how the substantially perpendicular extension 84 is attached to frame component 4*a* via a fastener 94, such as a rivet or bolt. FIG. 7 is a reverse perspective view of the detector assembly illustrated in FIG. 6, showing alternating inner support arm assemblies 50 and outer support arm assemblies 50'. It should be noted that more or less than eight detector assemblies may be used. The number of detector assemblies may range from two up to the number required to make a complete inspection. Alternatively, fewer detector assemblies could be used if the tubular member is able to be passed through apparatus of the invention more than once.

Figure 8:
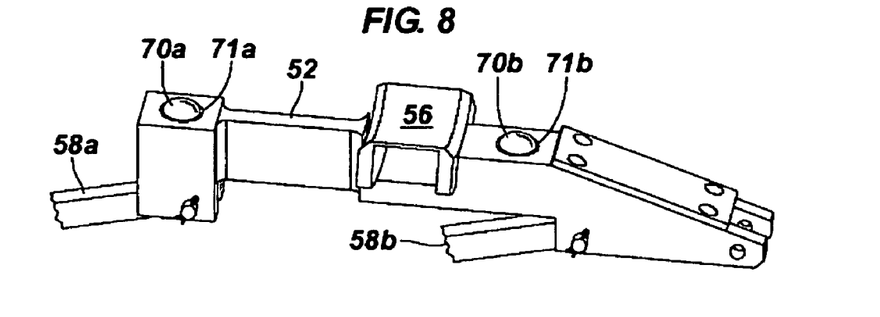
FIGS. 8-11 are perspective views of several non-limiting embodiments of the invention.
Figure 9:
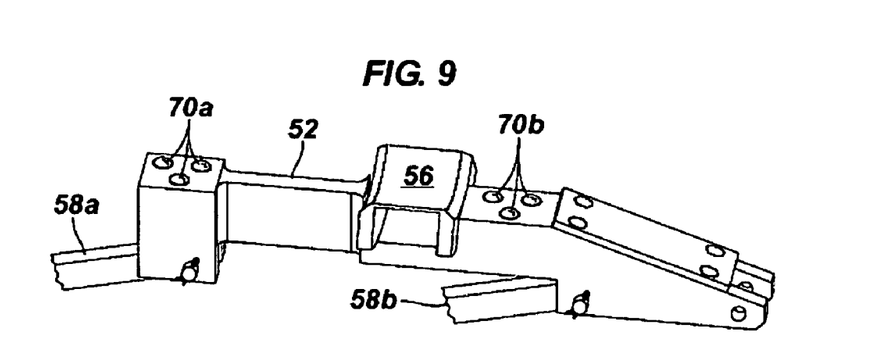
Figure 10:
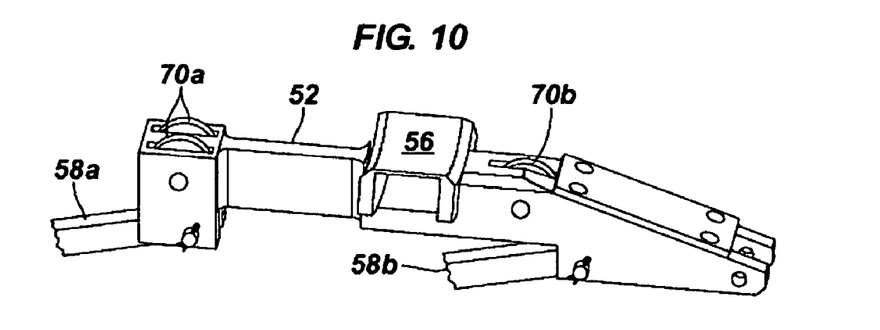
Figure 11:
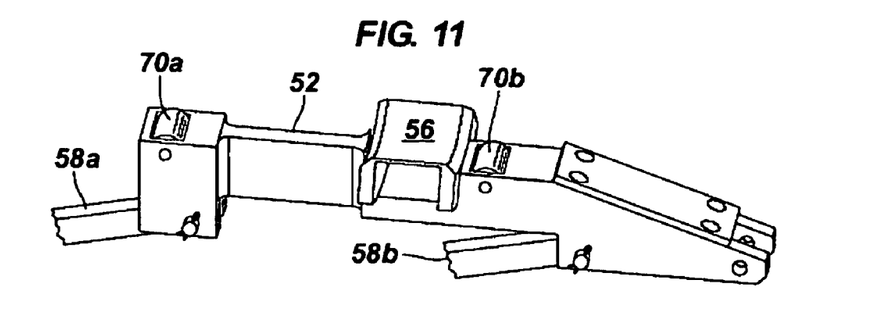

FIGS. 8-11 are perspective views of several non-limiting embodiments of embodiments of the invention, illustrating that the substantially frictionless members that function to maintain the magnetic detectors a first distance from the tubular member may take any number of forms. FIG. 8 illustrates substantially frictionless members 70*a* and 70*b* as ball bearings, which may be metallic or high strength plastic. Ball bearings are allowed to rotate in sockets 71*a* and 71*b* in primary support member 52 as the bearings traverse over a tubular member during inspection. FIG. 9 illustrates an alternative wherein three ball bearings 70*a* in respective sockets are employed on the front portion of primary support member 52 and three others 70*b* on the back end of primary support member 52. FIG. 10 illustrates two roller wheels 70*a*, similar to those illustrated in FIG. 3, in a front portion of primary support member 52, and a single roller wheel 70*b* in the back portion of primary support member 52. FIG. 11 illustrates use of two transverse rollers 70*a* and 70*b*. Those having ordinary skill in the art having the benefit of this disclosure will no doubt realize other functional alternatives to these specific embodiments, and these functional alternatives are deemed within the scope of the present invention.

FIGS. 12 and 13 illustrate an embodiment of the invention wherein all of the support arm sub-assemblies are the same. This arrangement does not allow for the magnetic flux from adjacent magnetic detectors to abut closely together, therefore allowing the possibility of small regions of magnetic flux to escape direct contact with a detector, but may still be sensitive enough for most applications, especially if the operator is experienced, and/or the operator has time to re-check the tubular member using slightly different positioning of detectors. Illustrated in FIGS. 12 and 13 are twelve detectors 56 adapted to be arranged around a tubular member (not shown) during an inspection. Note in FIG. 12 that there may be a gap "G" between adjacent detectors 56 when they are deployed around tubular member, which sacrifices a small amount of sensitivity when detecting defects. In other embodiments there may not be a gap G between detectors, and individual detectors 56 may actually touch their neighbors. FIG. 13 illustrates the embodiment of FIG. 12 in side elevation, providing another view of the detectors 56 and the slight gap G that might be present in between detectors 56.

Apparatus of the invention may be powered through pressurized fluids, such as compressed air, nitrogen, argon, and the like, including synthetic air such instrument air (air having most if its moisture removed). Depending on availability and/or the type of actuator assembly actually used in detecting the wide region of the tubular ember being inspected, apparatus of the invention may also be powered by battery, fuel cell, or other local power source. Certain embodiments may use only one or more solenoids to operate an actuator assembly.

One or more motors may be used that produce a linear stroke to move the primary support arms away from the secondary support arms. If motors are employed, an oil lubrication system may be used to protect and lubricate the motor, gears, and other mechanical parts. Alternatively, these parts may be comprised of frictionless coatings.

During an inspection operation, when it is desired to interrupt the inspection due to a wide spot in the tubular member, such as a coupling, or the tubular member has mud, paraffin, and/or other debris caked thereon, or for any reason, two optional manual switches may be provided, tripping open the bleeder valves and allowing wheels 20a and 20b to back away from the tubular member, and backing the detector assemblies away from the tubular member. Two other optional manual switches may be provided that allow the action of valve actuators 10a and 10b to be reversed, as when tubing being inspected is reversed in direction. The optional switches may be placed on a control panel for easy operator access.

While the apparatus and method embodiments of the invention have been described as using a pneumatic pressure, hydraulic pressure, motors or solenoids to operate the apparatus of the invention, the invention is not so limited. Any component or collection of components that function to allow selectively opening and closing the detector assemblies may be employed.

An alternative to the use of wheels on slides as part of the actuator may be the use of one or more optical sensors located near the tubular member to detect the presence of wide regions of the tubular member (or debris on the tubular member) traversing through the apparatus during an inspection procedure. The optical indicator may communicate its signal to the inspection sub-assemblies over a fiber optic line, wire line, wireless transmission, and the like. When a certain wide region is detected that would present a difficulty or hazard if allowed to reach the apparatus, the apparatus may be returned to its safe position with detectors retracted, long before the detected wide region creates a problem.

Typical uses of apparatus and methods of the invention will be in situations when it is desired to inspect tubing, pipe, or sucker rods in situ, as they are removed from a well bore. Alternatively, apparatus and methods of the invention may be used to inspect tubular members that are still in the warehouse, or which have been returned to a warehouse for inspection.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, no clauses are intended to be in the means-plus-function format allowed by 35 U.S.C. § 112, paragraph 6 unless "means for" is explicitly recited together with an associated function. "Means for" clauses are intended to cover the structures described herein as performing the recited function and not only structural equivalents, but also equivalent structures.

What is claimed is:

1. A tubular member inspection apparatus comprising:
   (a) a frame;
   (b) a magnetic coil and a detector assembly supported by the frame;
   (c) the frame, magnetic coil, and detector assembly each having inlet and outlet openings for passing a tubular member there through, the detector assembly having one or more magnetic detectors adapted to be spaced a first distance from the tubular member using one or more substantially frictionless members during an inspection; and
   (d) an actuator assembly comprising sensors adapted to sense wide portions of the tubular member and direct one or more actuators in the detector assembly to retract the detectors away from the tubular member a second distance greater than the first distance.

2. The apparatus of claim 1 wherein the one or more substantially frictionless members comprises one or more members selected from precision metal rollers, metal ball bearings, plastic rollers, ceramic balls, and non-rotating spacers in ball or roller shape.

3. The apparatus of claim 1 wherein the first distance is at least 0.030 inch.

4. The apparatus of claim 3 wherein the first distance ranges from about 0.050 inch up to about 0.5 inch.

5. The apparatus of claim 1 wherein the detector assembly comprises a plurality of detector support sub-assemblies.

6. The apparatus of claim 5 wherein each detector support sub-assembly comprises a primary and a secondary support member and one of the actuators, the primary support member adapted to support the one or more magnetic detectors, the primary support member moveably connected to the secondary support member through a dual linkage, the dual linkage allowing the detectors to be positioned substantially parallel to the tubular member when retracting away from and toward the tubular member.

7. The apparatus of claim 6 wherein the one or more substantially frictionless members comprises a pair of precision rollers in each primary support.

8. The apparatus of claim 6 wherein each actuator is selected from pneumatic, hydraulic, and electronic actuators.

9. The apparatus of claim 6 wherein the dual linkage comprises first and second links, each link having first and second ends, the first ends individually connected to the primary support member at first and second connections, and the second ends individually connected to the second support member at third and fourth connections.

10. The apparatus of claim 9 wherein the connections allow pivot movement between the links and the support members.

11. The apparatus of claim 1 wherein the second distance is at least sufficient to avoid damage to the detectors.

12. The apparatus of claim 1 wherein the sensors comprise a first rotating member riding on the tubular member upstream of the detector assembly and a second rotating member riding on the tubular member downstream of the detector assembly.

13. The apparatus of claim 5 wherein the plurality of detector support sub-assemblies comprises alternating outer detector support sub-assemblies and inner detector support sub-assemblies.

14. The apparatus of claim 13 wherein the outer detector support sub-assemblies each support a transverse magnetic detector and a wall thickness detector.

15. The apparatus of claim 13 wherein the detectors are selected from Hall elements, magneto diodes, and magneto resistors.

16. The apparatus of claim 13 wherein the inner detector support sub-assemblies each support a transverse magnetic detector, the detectors being selected from the group consisting of Hall elements, magneto diodes, and magneto resistors.

17. The apparatus of claim 12 wherein the actuator assembly comprises first and second valves, the first valve positioned upstream of the detector assembly and the second valve positioned downstream of the detector assembly.

18. The apparatus of claim 17 wherein the first and second valves are each spring-loaded, and each valve comprises a pressurized air inlet, a bleed air exhaust outlet, and the sensors are mounted on slide mechanisms adapted to slide into a position allowing a lever to bleed the air through the bleed air exhaust outlet when a wide portion of tubular member is sensed by one of the sensors, and wherein the valves are adapted to allow pressurized air into the actuators when the sensors do not sense a wide portion of tubular member.

19. The apparatus of claim 18 including an electronic circuit to synchronize the resetting of the air pressure in the actuators after the wide portion of tubular member has passed by the detectors and when the second sensor is reached.

20. The apparatus of claim 18 including pneumatic means to synchronize the resetting of the air pressure in the actuators after the wide portion of tubular member has passed by the detectors and when the second sensor is reached.

21. A tubular member inspection apparatus comprising:
 (a) a frame;
 (b) a magnetic coil, a detector assembly, and an actuator assembly supported by the frame;
 (c) the frame, magnetic coil, and detector assembly each having inlet and outlet openings for passing a tubular member there through, the detector assembly having one or more magnetic detectors adapted to be spaced a first distance from the tubular member using one or more substantially frictionless members during an inspection; and
 (d) the actuator assembly comprising sensors adapted to sense wide portions of the tubular member and direct one or more actuators in the detector assembly to retract the detectors away from the tubular member a second distance greater than the first distance.

22. A method of inspecting a tubular member comprising:
 (a) passing a tubular member through an apparatus, or driving the apparatus past the tubular member, the apparatus comprising
  i. a frame,
  ii. a magnetic coil; and
  iii. a detector assembly;
 (b) detecting variations in the magnetic field produced by defects in the tubular member, the detector assembly having one or more magnetic detectors spaced a first distance from the tubular member by one or more substantially frictionless members during; and
 (c) sensing a wide portion of the tubular member and directing one or more actuators in the detector assembly to retract the detectors away from the tubular member a second distance greater than the first distance.

23. The method of claim 22 wherein the variations in the magnetic field are detected by said magnetic detectors spaced so that their respective magnetic fields abut and provide a minimum of 100 percent inspection of the tubular member.

* * * * *